United States Patent
Smith

(10) Patent No.: US 8,202,290 B2
(45) Date of Patent: Jun. 19, 2012

(54) VISUAL OBTURATOR WITH HANDLE

(75) Inventor: Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 361 days.

(21) Appl. No.: 12/594,945

(22) PCT Filed: Apr. 15, 2008

(86) PCT No.: PCT/US2008/060307
§ 371 (c)(1),
(2), (4) Date: Oct. 7, 2009

(87) PCT Pub. No.: WO2008/130904
PCT Pub. Date: Oct. 30, 2008

(65) Prior Publication Data
US 2010/0137895 A1    Jun. 3, 2010

Related U.S. Application Data

(60) Provisional application No. 60/925,108, filed on Apr. 17, 2007.

(51) Int. Cl.
*A61B 17/34* (2006.01)
(52) U.S. Cl. .................................................. 606/185
(58) Field of Classification Search .................. 606/185, 606/167, 170, 190; 600/184, 114, 104, 106; 604/164.01, 164.06, 164.1, 164.11, 164.12
See application file for complete search history.

(56) References Cited

U.S. PATENT DOCUMENTS

| | | |
|---|---|---|
| 3,760,810 A | 9/1973 | Van Hoorn |
| 4,878,485 A | 11/1989 | Adair |
| 5,169,397 A | 12/1992 | Sakashita et al. |
| 5,250,068 A | 10/1993 | Ideguchi et al. |
| 5,271,380 A | 12/1993 | Riek et al. |
| 5,290,276 A | 3/1994 | Sewell, Jr. |
| 5,334,150 A | 8/1994 | Kaali |
| 5,354,302 A | 10/1994 | Ko |
| 5,376,076 A | 12/1994 | Kaali |
| 5,380,291 A | 1/1995 | Kaali |
| 5,385,572 A | 1/1995 | Nobles et al. |
| 5,431,151 A | 7/1995 | Riek et al. |
| 5,441,041 A | 8/1995 | Sauer et al. |
| 5,445,142 A | 8/1995 | Hassler, Jr. et al. |
| 5,467,762 A | 11/1995 | Sauer et al. |
| 5,551,947 A | 9/1996 | Kaali |

(Continued)

FOREIGN PATENT DOCUMENTS

EP    0664992    8/1995

(Continued)

*Primary Examiner* — Elizabeth Houston

(57) ABSTRACT

A trocar system includes an obturator handle defining a handle axis and having an axial bore and an obturator cartridge adapted for releasable mounting to the obturator handle. The obturator cartridge includes a cartridge frame and an elongate obturator extending from the cartridge frame and at least partially positionable within the axial bore of the obturator handle. The elongate obturator includes an image transmitting member and having an obturator blade mounted adjacent the image transmitting member. The obturator blade is adapted for movement relative to the image transmitting member between an initial condition and a deployed position. A trigger is mounted to the obturator handle and adapted for releasable operative coupling to the obturator blade. The trigger is movable to cause movement of the obturator blade from at least the initial condition to the deployed position thereof. The obturator cartridge includes a longitudinal opening extending through the cartridge frame and the elongate obturator. The longitudinal opening is adapted to receive an endoscope.

9 Claims, 13 Drawing Sheets

U.S. PATENT DOCUMENTS

| | | | |
|---|---|---|---|
| 5,562,696 A | 10/1996 | Nobles et al. |
| 5,569,160 A | 10/1996 | Sauer et al. |
| 5,569,291 A | 10/1996 | Privitera et al. |
| 5,569,292 A | 10/1996 | Scwemberger et al. |
| 5,591,192 A | 1/1997 | Privitera et al. |
| 5,609,562 A | 3/1997 | Kaali |
| 5,632,717 A | 5/1997 | Yoon |
| 5,658,236 A | 8/1997 | Sauer et al. |
| 5,658,306 A | 8/1997 | Kieturakis et al. |
| 5,662,673 A | 9/1997 | Kieturakis |
| 5,674,184 A | 10/1997 | Hassler, Jr. |
| 5,685,820 A | 11/1997 | Riek et al. |
| 5,720,761 A | 2/1998 | Kaali |
| 5,797,944 A | 8/1998 | Nobles et al. |
| 5,817,061 A | 10/1998 | Goodwin et al. |
| 5,860,996 A | 1/1999 | Urban et al. |
| 5,980,549 A | 11/1999 | Chin |
| RE36,434 E | 12/1999 | Hamlin et al. |
| 6,007,481 A | 12/1999 | Riek et al. |
| 6,203,557 B1 | 3/2001 | Chin |
| 6,206,823 B1 | 3/2001 | Kolata et al. |
| 6,685,630 B2 | 2/2004 | Sauer et al. |
| 7,023,423 B2 | 4/2006 | Rosenberg |
| 7,041,115 B2 | 5/2006 | Mirza et al. |
| 7,074,180 B2 | 7/2006 | Bertolero et al. |
| 7,322,933 B2 | 1/2008 | Sauer et al. |
| 7,470,230 B2 | 12/2008 | Smith et al. |
| 2002/0143236 A1 | 10/2002 | Sauer et al. |
| 2004/0015182 A1 | 1/2004 | Kieturakis et al. |
| 2005/0065543 A1 | 3/2005 | Kahle et al. |
| 2005/0261717 A1 | 11/2005 | Sauer et al. |
| 2006/0079925 A1 | 4/2006 | Kerr |
| 2006/0224174 A1 | 10/2006 | Smith et al. |
| 2007/0016237 A1 | 1/2007 | Smith |
| 2007/0276191 A1 | 11/2007 | Selover et al. |
| 2008/0009894 A1 | 1/2008 | Smith |

FOREIGN PATENT DOCUMENTS

| | | |
|---|---|---|
| EP | 0684016 | 11/1995 |
| EP | 0815796 | 1/1998 |
| EP | 1994897 | 11/2008 |
| WO | 9513751 | 5/1995 |
| WO | 2004002337 | 1/2004 |

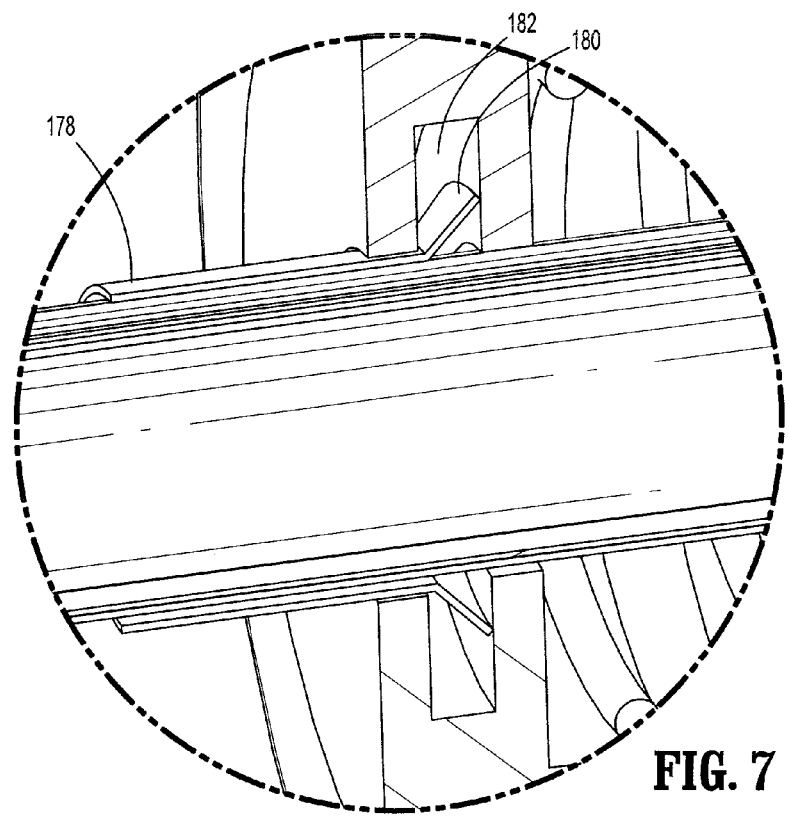
FIG. 7
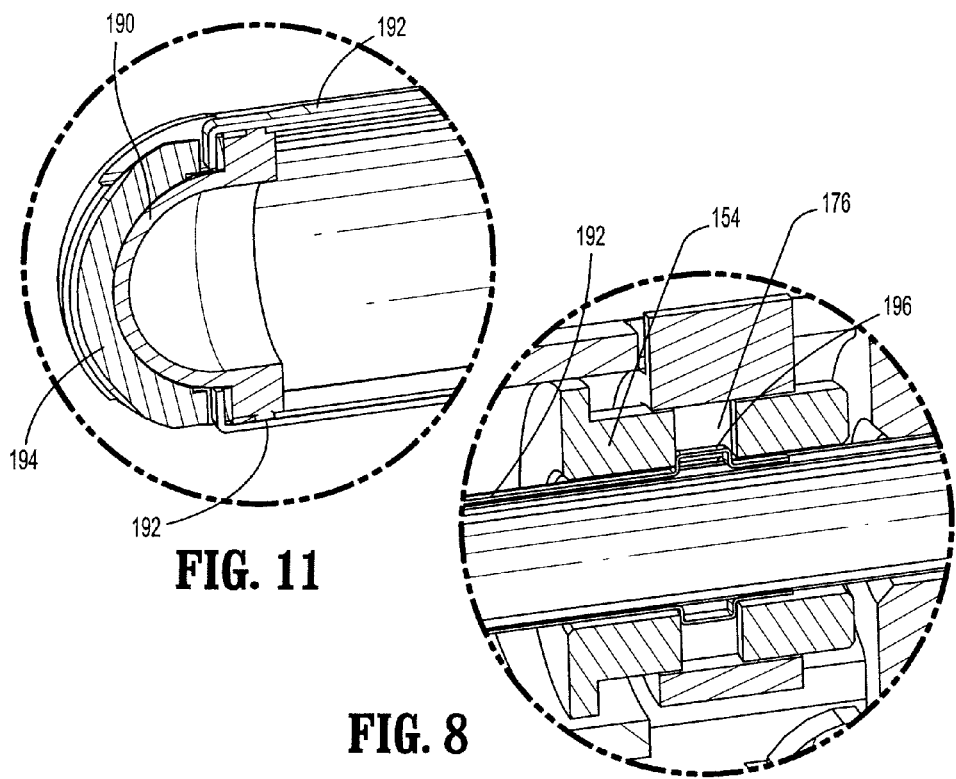
FIG. 11
FIG. 8

VISUAL OBTURATOR WITH HANDLE

CROSS REFERENCE TO RELATED APPLICATIONS

This application is a National Stage Application of PCT/US2008/060307 filed Apr. 15, 2008 under 35 USC §371 (a), which claims priority of U.S. Provisional Patent Application Ser. No. 60/925,108 filed Apr. 17, 2007 the entire contents of which are hereby incorporated by reference.

BACKGROUND

1. Technical Field

The present disclosure relates to an apparatus for penetrating body tissue. More particularly, the present disclosure relates to a trocar system including an obturator capable of receiving an endoscope to provide visual observation during penetration of the peritoneum or other body tissue.

2. Description of the Related Art

Endoscopic surgical procedures, i.e., surgical procedures performed through tubular sleeves or cannulas have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through a small incision or through narrow endoscopic tubes (cannulas) inserted through small entrance wounds in the skin. In laparoscopic procedures surgery is performed in the interior of the abdomen.

Laparoscopic procedures generally utilize instrumentation that is internally sealed to inhibit gases from entering or exiting the body through the laparoscopic or endoscopic incision. This is particularly true in surgical procedures in which the surgical region is insufflated. Moreover, laparoscopic and endoscopic procedures often require the surgeon to act on organs, tissues and vessels far removed from the incision, thereby requiring that any instruments to be used in such procedures be of sufficient size and length to permit remote operation. Typically, after the surgical region is insufflated, trocars are used to puncture the body cavity and include a cannula which remains in place for use during endoscopic procedures. Generally, trocars used during such procedures include a stylet having a sharp tip for penetrating the body cavity positioned coaxially within protective tubes to protect a patient or surgeon from inadvertent contact with the tip. An example of a known trocar is described in commonly assigned, U.S. Pat. No. 4,601,710 to Moll. Most currently used trocars rely on protective tubes or relative retraction of the tip to prevent inadvertent contact with tissue.

The present disclosure relates to a trocar system for observing the penetration of the peritoneum or other body portions.

SUMMARY

A trocar system includes an obturator handle defining a handle axis and having an axial bore and an obturator cartridge adapted for releasable mounting to the obturator handle. The obturator cartridge includes a cartridge frame and an elongate obturator extending from the cartridge frame and at least partially positionable within the axial bore of the obturator handle. The elongate obturator includes an image transmitting member and having an obturator blade mounted adjacent the image transmitting member. The obturator blade is adapted for movement relative to the image transmitting member between an initial condition and a deployed position. A trigger is mounted to the obturator handle and adapted for releasable operative coupling to the obturator blade. The trigger is movable to cause movement of the obturator blade from at least the initial condition to the deployed position thereof. The obturator cartridge includes a longitudinal opening extending through the cartridge frame and the elongate obturator. The longitudinal opening is adapted to receive an endoscope.

The cartridge frame of the obturator cartridge includes a firing member operatively engageable with the obturator blade and with the trigger. The firing member is normally biased in a firing direction corresponding to the deployed condition of the obturator blade. The trigger includes a latch adapted to restrain the firing member in a first position corresponding to the initial condition of the obturator blade and wherein movement of the trigger causes release of the latch from the firing member to thereby permit the firing member to move in the firing direction toward a second position thereof. The cartridge frame may include a firing spring operatively couplable with the firing member and adapted to bias the firing member in the firing direction. A return spring is disposed within the cartridge frame, and positioned to engage the firing member upon movement of the firing member in the firing direction to the second position thereof. The return spring is adapted to bias the firing member in a return direction opposed to the firing direction and to the first position of the firing member. The latch of the trigger is adapted to releasably couple with the firing member upon return thereof to the first position.

BRIEF DESCRIPTION OF THE DRAWINGS

The preferred embodiments of the invention are described hereinbelow with reference to the drawings wherein:

FIG. 7 is an enlarged view of the area of detail depicted in FIG. 5;

FIG. 8 is an enlarged view of the area of detail depicted in FIG. 5;

FIG. 11 is an enlarged view of the area of detail depicted in FIG. 5;

DETAILED DESCRIPTION OF THE PREFERRED EMBODIMENTS

Figure 1:
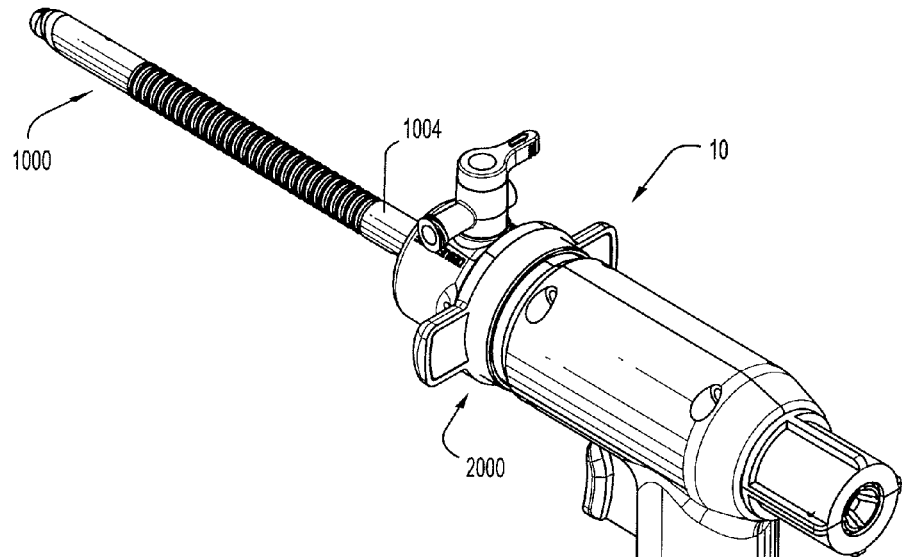
FIG. 1 is a perspective view of a trocar system in accordance with the principles of the present disclosure illustrating the cannula assembly and the obturator assembly positioned within the cannula assembly.
Figure 2:
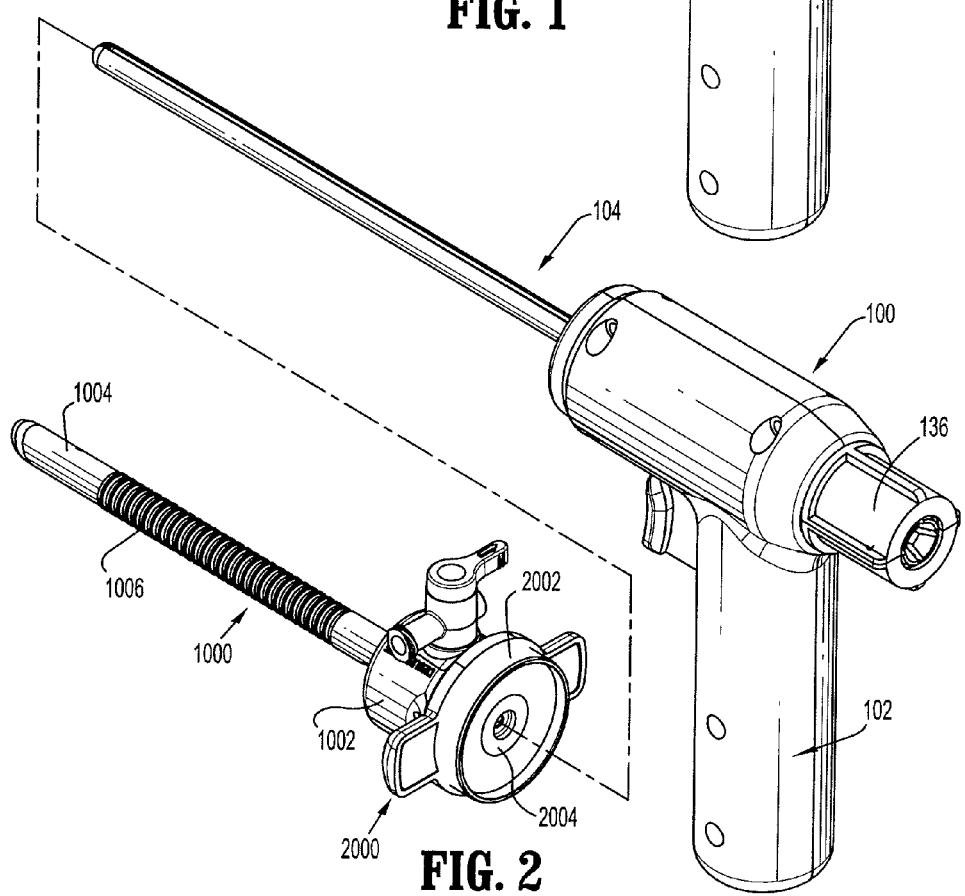
FIG. 2 is a perspective view of the trocar system illustrating the obturator assembly removed from the cannula assembly.

Referring now in detail to the drawing figures, in which, like references numerals identify similar or identical elements, there is illustrated, in FIGS. 1 and 2, a trocar system constructed in accordance with a preferred embodiment of the present disclosure and designated generally by reference numeral 10. Trocar system 10 is particularly adapted for use in minimally invasive surgical procedures such as endoscopic or laparoscopic procedures. Trocar system 10 is adapted to penetrate body tissue, e.g., the abdominal wall, and to provide a simultaneous forward directional view of the body tissue. Generally, trocar system 10 includes two principal subassemblies, namely, obturator assembly 100 and cannula assembly 1000.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be transparent in part, or in whole, and may be fabricated from biocompatible metal or polymeric material. Cannula assembly 1000 may include an internal seal such as a duck-bill valve or other zero closure valve adapted to close in the absence of a surgical instrument to prevent passage of insufflation gases through the cannula assembly 1000. Cannula sleeve 1004 may include a plurality of annular ribs 1006 to facilitate retention of the cannula sleeve 1004 within tissue.

Trocar system 10 may also include a seal assembly 2000 which is preferably releasably mounted to cannula housing 1002. Means for releasably connected seal assembly 2000 to cannula housing 1002 may include a bayonet coupling, threaded connection, latch, friction fit, tongue and groove arrangements, snap-fit, etc. Seal assembly 2000 includes seal housing 2002 and at least one internal seal 2004 which is adapted to form a fluid tight seal about an instrument inserted through the seal assembly 2000. One suitable seal may be the fabric seal disclosed in commonly assigned U.S. Pat. No. 6,702,787, which issued Mar. 9, 2004, the entire contents of which are incorporated herein by reference. The seal disclosed in the '630 patent may be a flat septum seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

Figure 3:
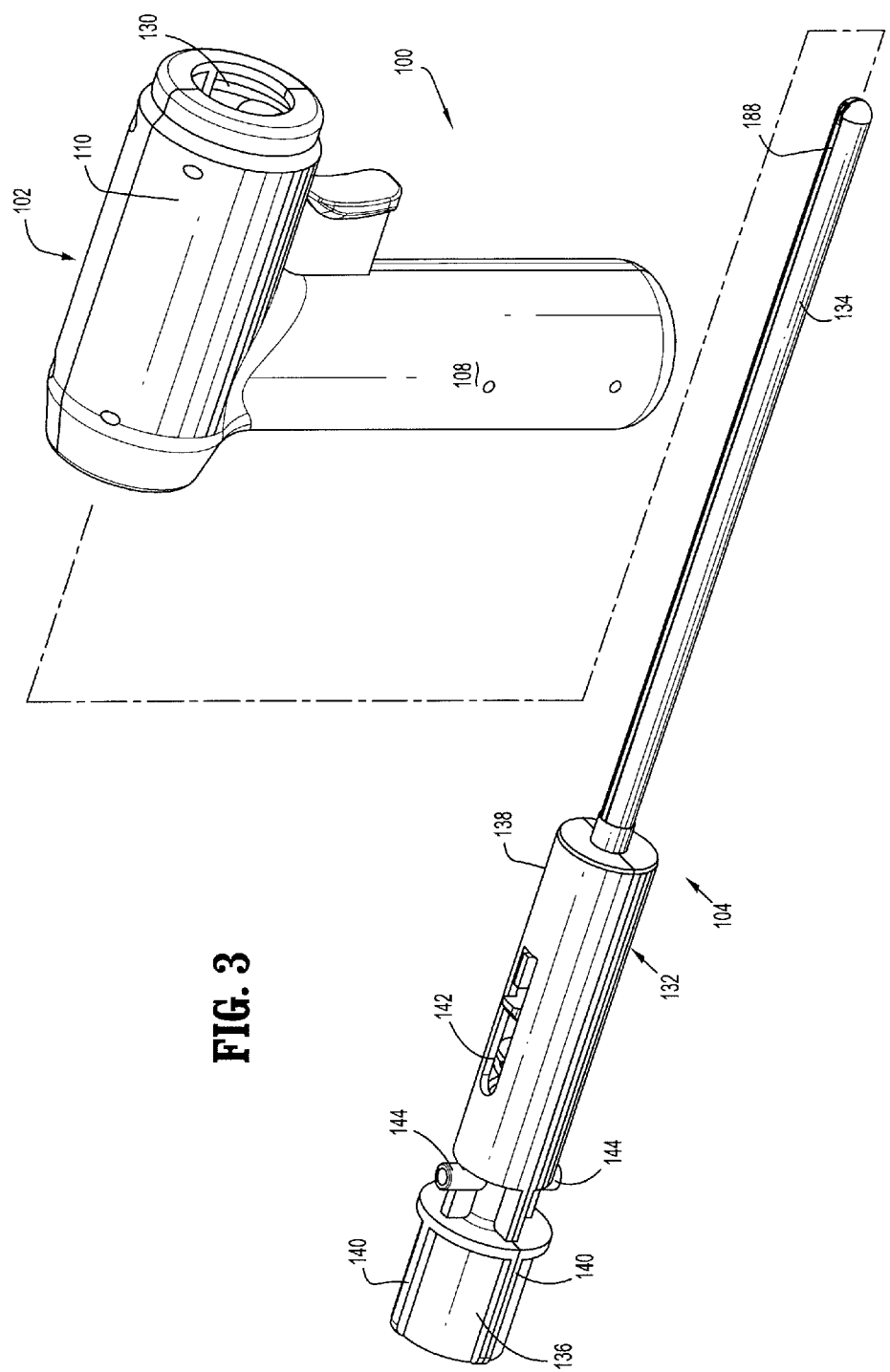
FIG. 3 is a perspective view of the obturator assembly illustrating the obturator handle and the obturator cartridge removed from the obturator handle.
Figure 4:
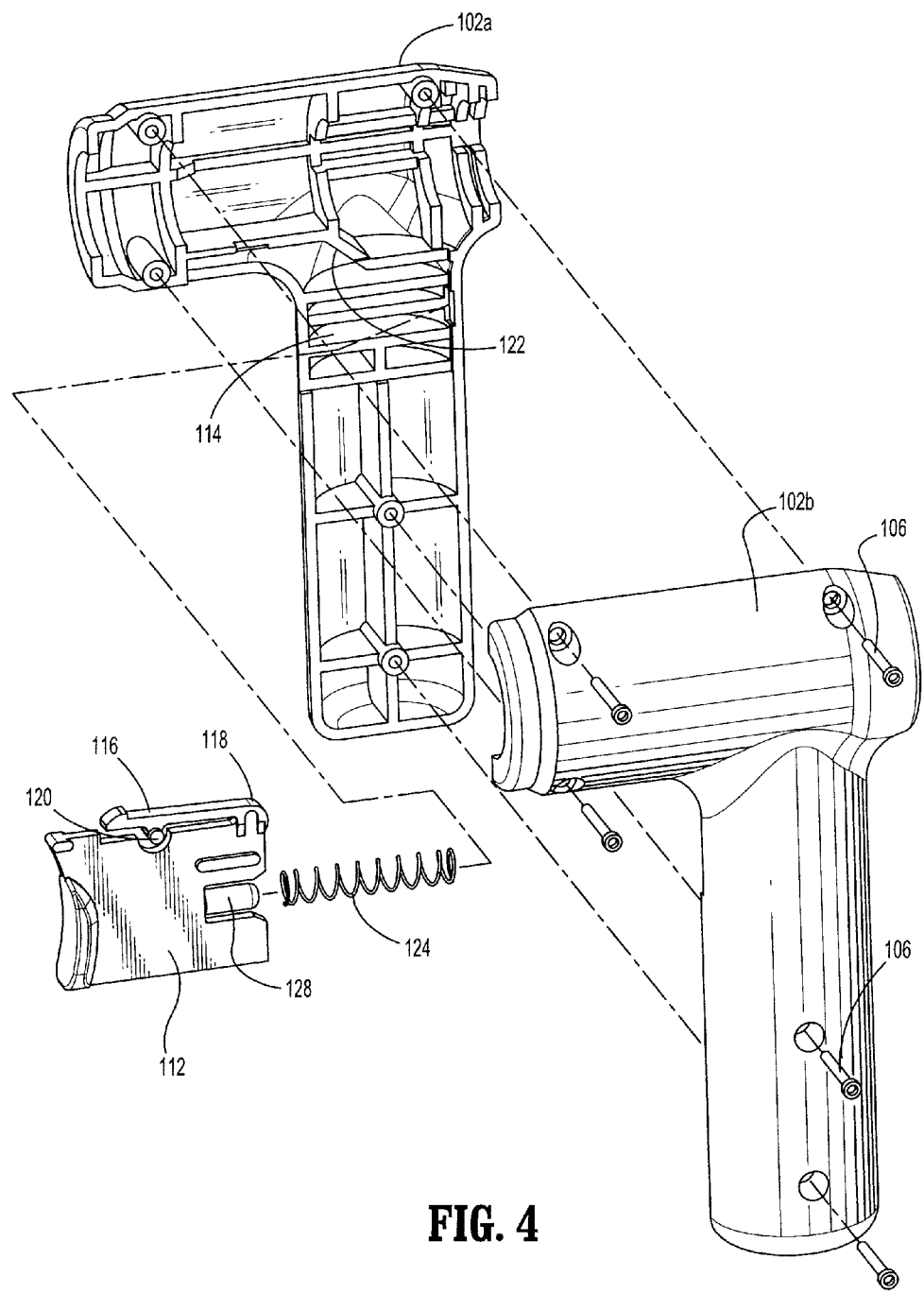
FIG. 4 is a perspective view with parts separated of the handle of the obturator assembly.
Figure 5:
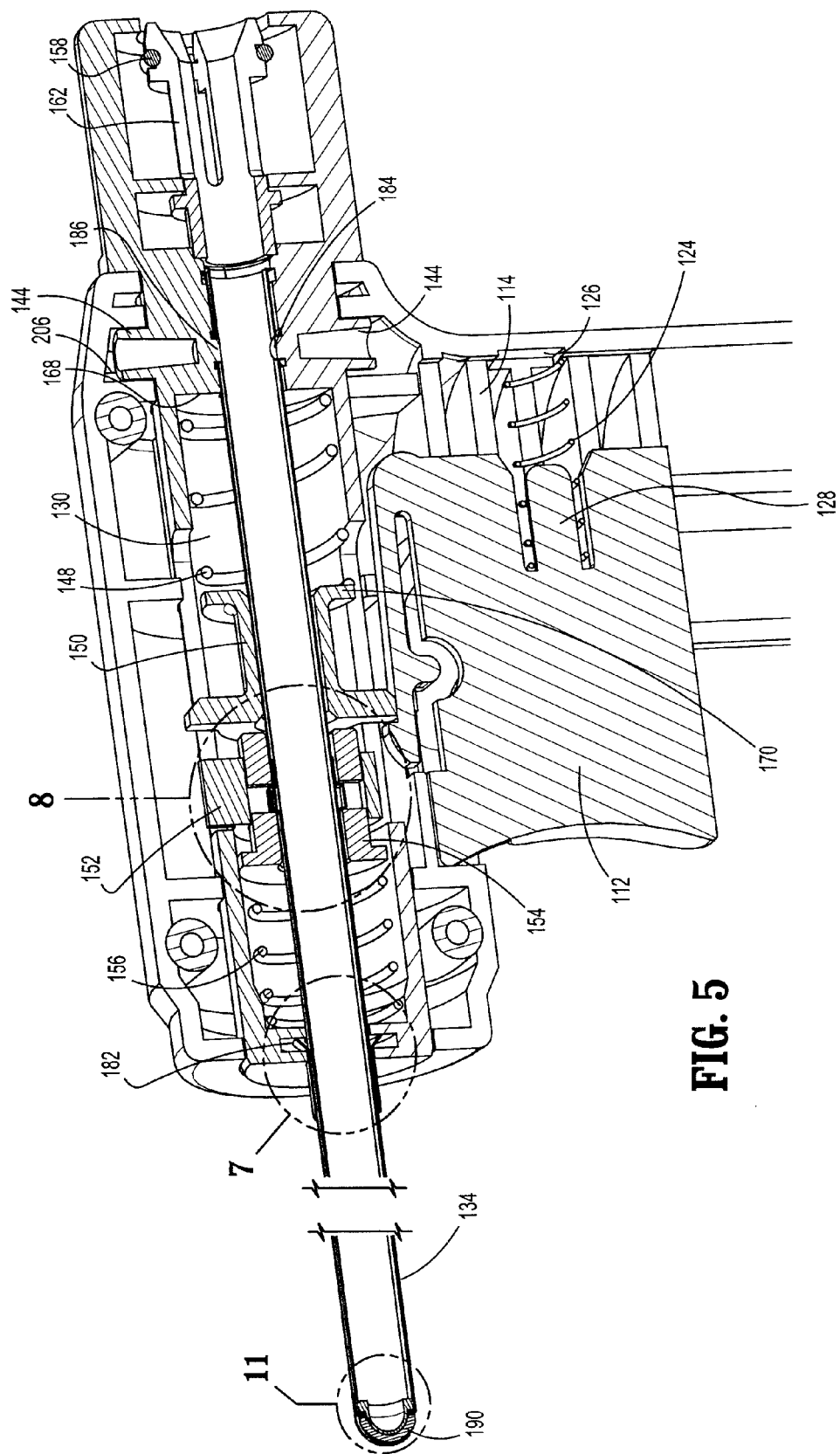
FIG. 5 is a perspective view in partial cross-section illustrating the obturator cartridge mounted within the obturator handle of the obturator assembly.

Referring to FIGS. 2-4, in conjunction with the cross-sectional view of FIG. 5, obturator assembly 100 includes obturator handle 102 and obturator cartridge 104 which is adapted for releasable mounting to the obturator handle 102. Obturator handle 102 includes handle half sections 102a, 102b connected to each other via screw means 106, adhesives, cements or the like. Obturator handle 102 defines pistol or hand grip 108 and barrel 110. Obturator handle 102 further includes trigger 112 which is mounted within recess 114 defined within the obturator handle 102. Trigger 112 is adapted for reciprocal longitudinal movement relative to obturator handle 102. Trigger 112 includes latch 116 which is adapted to pivot about fulcrum 118. Latch 116 includes cam pin 120 which is received beneath cam shelf 122 of obturator handle 102. Upon rearward or proximal movement of trigger 112, cam pin 120 rides beneath cam shelf 122 causing latch 116 to pivot downwardly about fulcrum 118. Trigger 112 is normally biased in a distal direction by coil spring 124. At its proximal end, coil spring 124 engages interior surface 126 of obturator handle 102 and, at its distal end, is received about spring mount 128 of trigger 112. Barrel 110 of obturator handle 102 defines longitudinal bore 130 extending therethrough.

Figure 6:
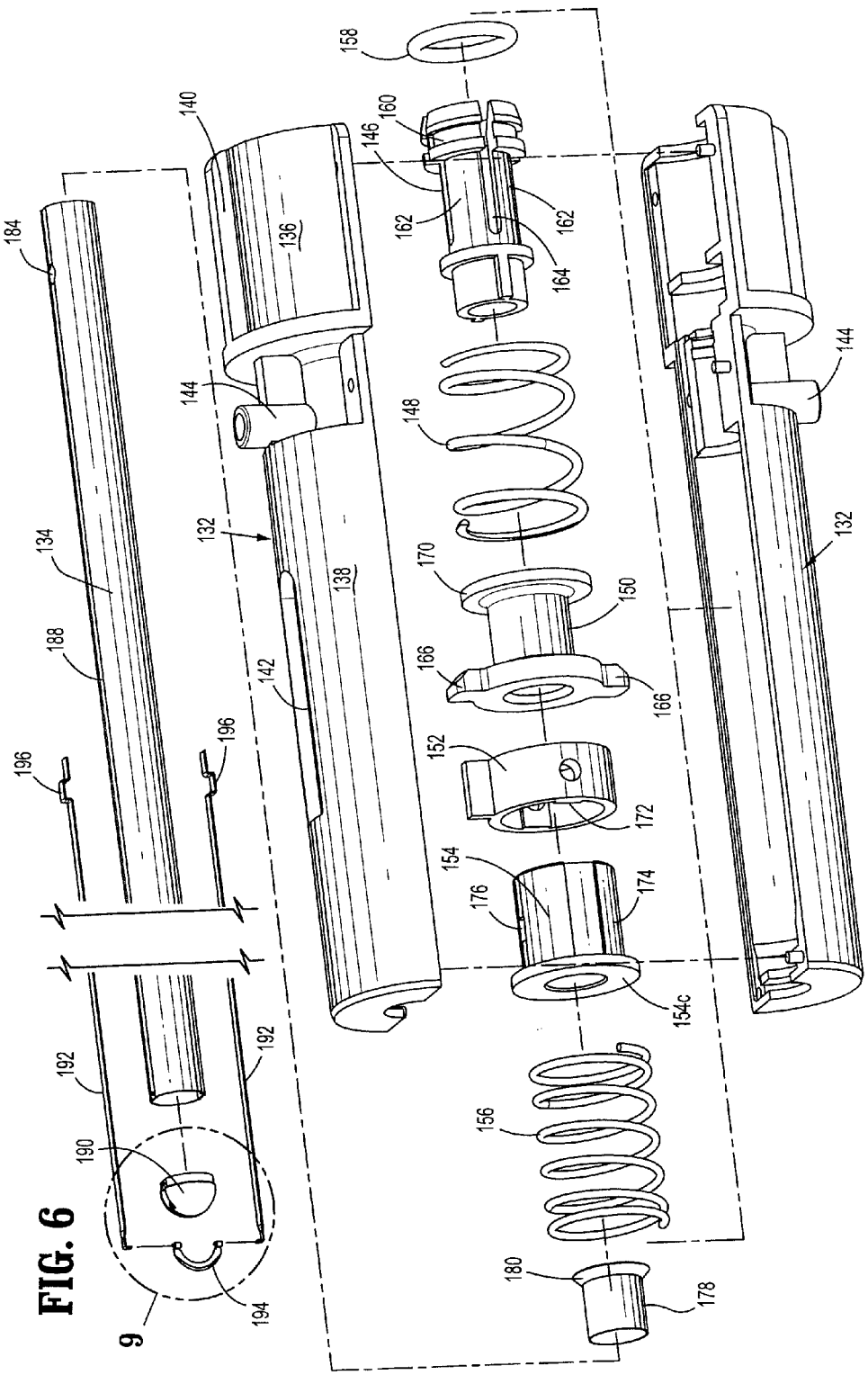
FIG. 6 is a perspective view with parts separated of the obturator cartridge of the obturator assembly.

Referring now to FIGS. 3, 5 and 6 obturator cartridge 104 will be discussed. Obturator cartridge 104 is adapted for at least partial insertion through longitudinal bore 130 of obturator handle 102, and provides penetration and visual capabilities to trocar system 10. Obturator cartridge 104 may be intended for disposal, or possibly, for resterilization, subsequent to its use, and, according is releasably mountable to obturator handle 102. Moreover, obturator cartridge 104 may be intended to be removed from obturator handle 102 whereby after use another obturator cartridge 104 may be mounted to obturator handle 102 for subsequent use.

Obturator cartridge 104 includes cartridge frame 132 and elongate obturator member 134 extending from the cartridge frame 132. Cartridge frame 132 includes proximal collar 136 and cylindrical portion 138 extending from the proximal collar 136. Proximal collar 136 includes longitudinal ribs 140 for facilitating engagement by the clinician. Cylindrical portion 138 includes at least one longitudinal slot 142, preferably, two longitudinal slots 142 in diametrical opposed relation, in its outer wall. Cartridge frame 132 further defines external locking lugs 144 in diametrical opposed relation to facilitate releasable mounting of cartridge frame 132 to obturator handle 102 as will be discussed.

Referring to FIGS. 5 and 6, cartridge frame 132 of obturator cartridge 104 includes, from proximal to distal, scope retainer 146, hammer spring 148, hammer 150, stop 152, driver holder 154, return spring 156. Scope retainer 146 is mounted within cartridge frame 132 and incorporates O-ring spring 158. In particular, O-ring spring 158 is received within peripheral slot 160 of scope retainer 146. Scope retainer 146 defines a plurality of proximal legs 162 separated by slots 164. Proximal legs 162 may move radially outwardly to receive an instrument, e.g., an endoscope, in frictional relation therewith. O-ring spring 158 is adapted to bias proximal legs 162 of scope retainer 146 radially inwardly to the position shown in FIG. 5. In this position, the interior surfaces of proximal legs 162 may establish a frictional relation with the inserted object.

Hammer 150 of obturator cartridge 104 is adapted for reciprocal longitudinal movement within cartridge frame 132. Hammer 156 includes diametrically opposed tabs 166 which extend through longitudinal slots 142 of cartridge frame 132, and are each adapted to engage latch 116 of trigger 112 when in an initial position of the trigger 112 depicted in FIG. 5. Hammer 150 is biased in a distal direction through hammer spring 148. Specifically, hammer spring 148 engages interior surface 168 of cartridge frame 132 and engages proximal end face 170 of hammer 150.

Stop 152 of obturator cartridge 104 is fixed within cartridge frame 132 and defines central opening 172 for at least partial reception of driver holder 154. Stop 152 limits the range or degree of longitudinal movement of hammer 150. Stop 152 is coaxially mounted about driver holder 154 in a manner to permit the driver holder 154 to advance and retract within bore 172 of the stop 152. Driver holder 154 defines a central cylinder 174 having a pair of opposed slots 176 at least partially extending through the wall of the central cylinder 174. Driver holder 154 is normally biased in a proximal direction by driver return spring 156 which engages both an interior surface of cartridge frame 132 and distal collar 154c of driver holder 154. Cartridge frame 132 further includes port seal opener 178 extending distally from the cartridge frame 132. In one embodiment, port seal opening 178 includes proximal flange 180 which is received within corresponding mounting recess 182 of cartridge frame 132 as best depicted in FIG. 7. Post seal opening 178 is adapted to penetrate and/or open seal 2004 of seal assembly 2000 of cannula assembly 1000.

With continued reference to FIGS. 5 and 6, elongated obturator member 134 of obturator cartridge 104 is securely mounted within cartridge frame 132. In one method, obturator member 134 includes diametrical openings 184 adjacent its proximal end. Openings 184 receive internal locking tabs 186 of cartridge frame 132, e.g., in snap relation therewith to secure the two components. Obturator member 134 may be a scope tube and defines a longitudinal passage for accommodating in endoscope. Obturator member 134 may define a pair of opposed longitudinal grooves 188 in its outer surface extending to the distal end of the obturator member 134. Obturator member 134 has image transmitting member 190 mounted to its distal end. In one embodiment, image transmitting member 190 is adhered to obturator member 134. Image transmitting member 190 may be a transparent optical window fabricated from a variety of materials such as polystyrene, polymethyl-methylaceylate (PMMA), polyurethane, transparent epoxies and/or glass or transparent materials. Image transmitting member 190 may define a semi-hemispherical configuration. Alternately, image transmitting member 190 may be an image directing member in the form of, e.g., a lens, an optical prism, an optical mirror, or like image directing medium.

Referring now to FIGS. 5-6 and 8-10, obturator cartridge 104 includes a tissue penetrating assembly in the form of blade drivers 192 and cutting blade 194 which is mounted to the distal end of the blade drivers 192. In one embodiment, two blade drivers 192 extend along obturator member 134 and are received within longitudinal grooves 188 of the obturator member 134. As best depicted in FIG. 8, the proximal ends of blade drivers 192 include offset portions 196 which are received within driver holder 154, specifically, within grooves 176 of the driver holder 154, thereby securing the blade drivers 192 to the driver holder 154. Accordingly, longitudinal movement of driver holder 154 causes corresponding longitudinal movement of blade drivers 192 and cutting blade 194.

Figure 9:
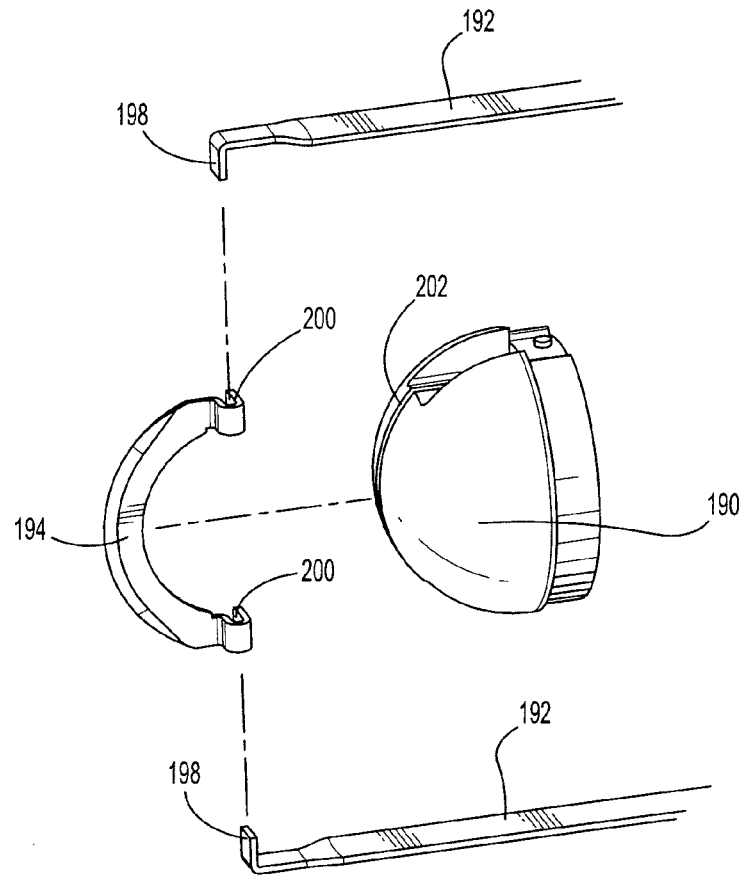
FIG. 9 is an enlarged view of the area of detail depicted in FIG. 6.
Figure 10:
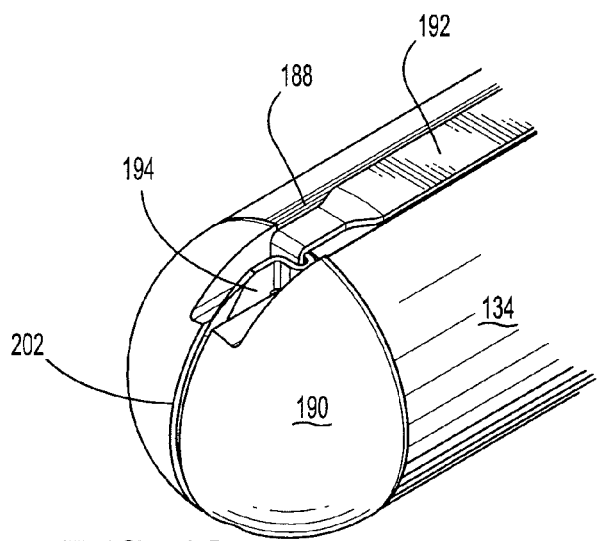
FIG. 10 is an enlarged view of the image transmitting member and the obturator blade.

Referring now to FIGS. 9-11, cutting blade 194 is secured to blade drivers through corresponding reception of mounting hooks 198 of blade drivers 192 within u-shaped recesses 200 of cutting blade 194. Cutting blade 194 is at least partially accommodated within groove 202 of image transmitting member 190 and moves within the groove 202 between a non-deployed position and a deployed position. Cutting blade 194 may define a sharpened cutting edge or alternatively, may be relatively blunt to be atraumatic to tissue. Cutting blade 194 may be formed of a suitable rigid material such as stainless steel or titanium, or alternatively, may be fabricated of a suitable polymeric material. Cutting blade 194 is preferably centered with respect to the outer surface of the image transmitting member 190 as shown. Thus, in visualization, cutting blade 194 is seen as a thin line through the center, i.e. bisecting, the viewing field so as not to obstruct viewing of the body.

Figure 13:
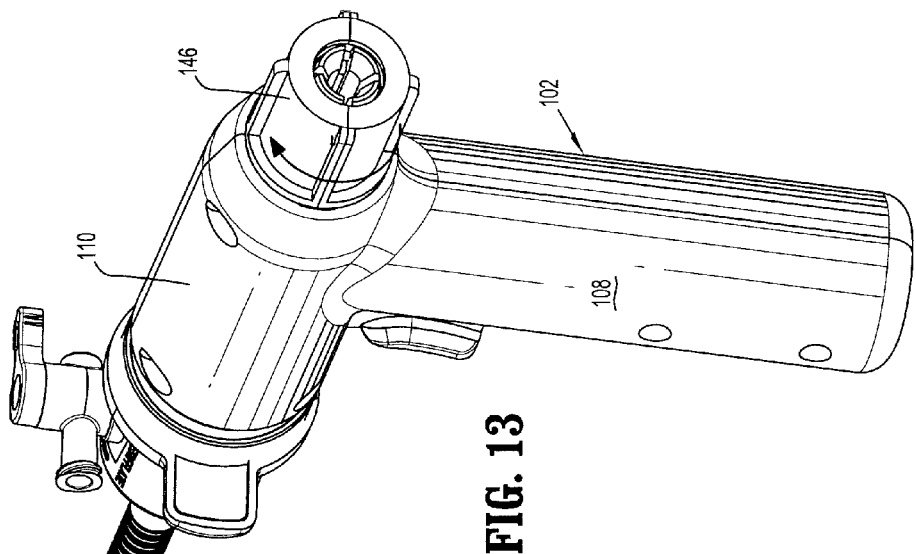
FIG. 13 is a perspective view illustrating the obturator cartridge mounted within the obturator handle.
Figure 12:
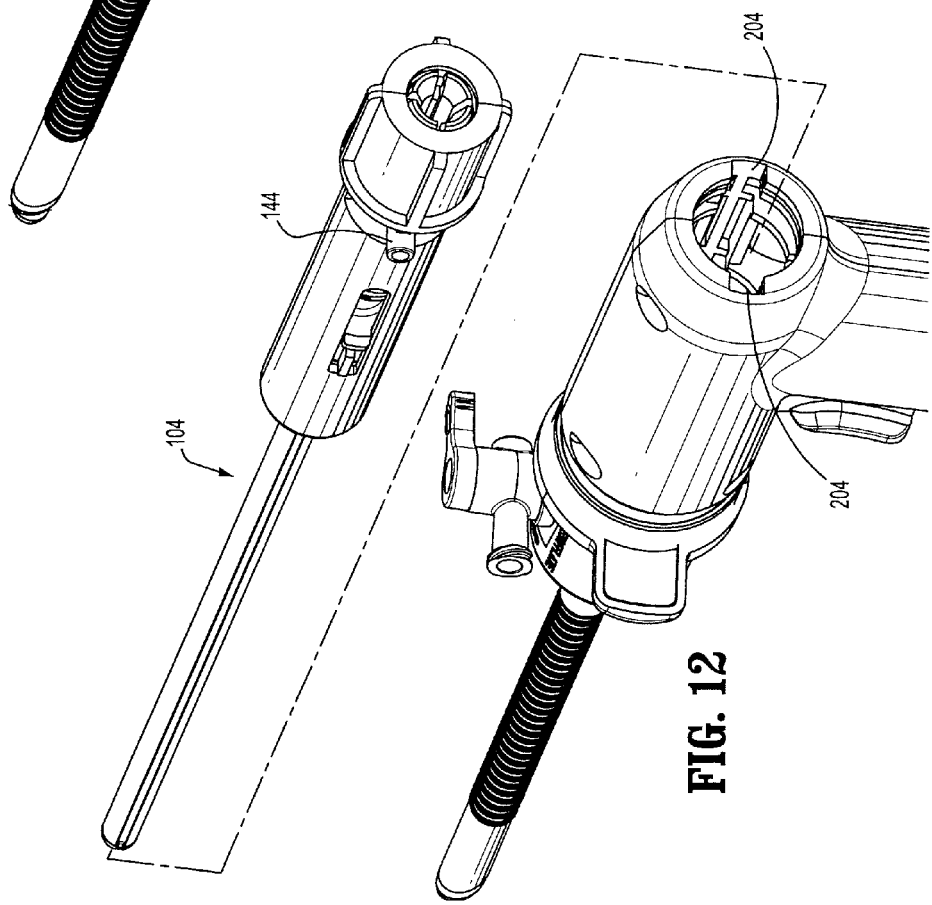
FIG. 12 is a perspective view of the obturator cartridge prior to mounting within the obturator handle.

FIGS. 12-13 illustrate one arrangement for releasably mounting obturator cartridge 104 within obturator handle 102 is illustrated. As indicated hereinabove, cartridge frame 132 includes external locking lugs 144 arranged in diametrical opposed relation. Obturator handle 102 includes corresponding lug receiving recesses 204 adjacent its proximal face. Upon assembly of obturator cartridge 104 within obturator handle 102, locking lugs 144 are aligned with locking recesses 204 and advanced therewithin. Thereafter, cartridge frame 132 is rotated in a clockwise direction where locking lugs 144 are received within locking slots 206 of obturator handle 102 to releasably secure the two components (FIG. 5). Obturator cartridge 104 is symmetrically arranged about its longitudinal axis "k". Accordingly, obturator cartridge 104 may be introduced within obturator handle 102 without concern of alignment of a particular locking lug 144 of the cartridge 104 with a locking recess 204 of the handle 102.

Upon securing obturator cartridge 104 within obturator handle 102, hammer 150 is engaged by trigger 112, e.g., latch 116 of the trigger 112 in the aforedescribed manner. Moreover, either tab 166 of hammer 150 (depending on the rotational orientation of cartridge frame 132) will be engaged by latch 116 of trigger 112 through a corresponding longitudinal slot 142 of cartridge frame 132.

Figure 14:
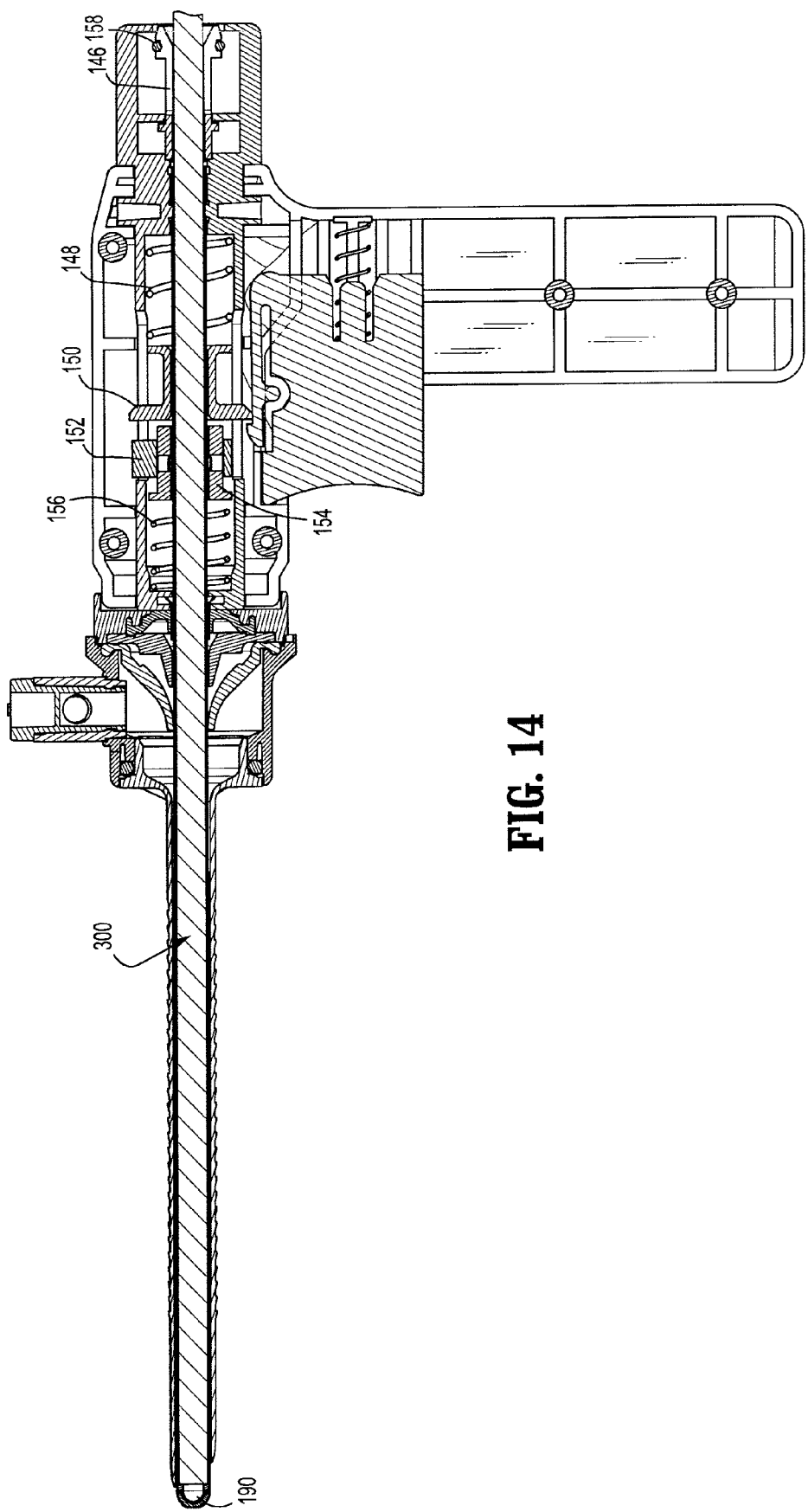
FIG. 14 is a side cross-sectional view of the trocar system illustrating an endoscope positioned within the obturator assembly.

FIG. 14 illustrates trocar system fully assembled and in cross-section with an endoscope 300 positioned within obturator handle 102 and within obturator cartridge 104. One suitable endoscope 300 which may be used with trocar system 10 is disclosed in commonly assigned U.S. Pat. No. 5,412,504 to Leiner, the entire contents of which disclosure are hereby incorporated by reference. Endoscope 300 may be any conventional scope suitable for endoscopic applications including, e.g., a laparoscope, arthroscope, colonoscope, etc. Endoscope 300 incorporates an optical train or lens arrangement which is capable of transmitting an image of an object from the distal or objective lens through the eyepiece or monitor for viewing by the surgeon. Further details of endoscope 300 may be ascertained by reference to the '504 patent.

Figure 15:
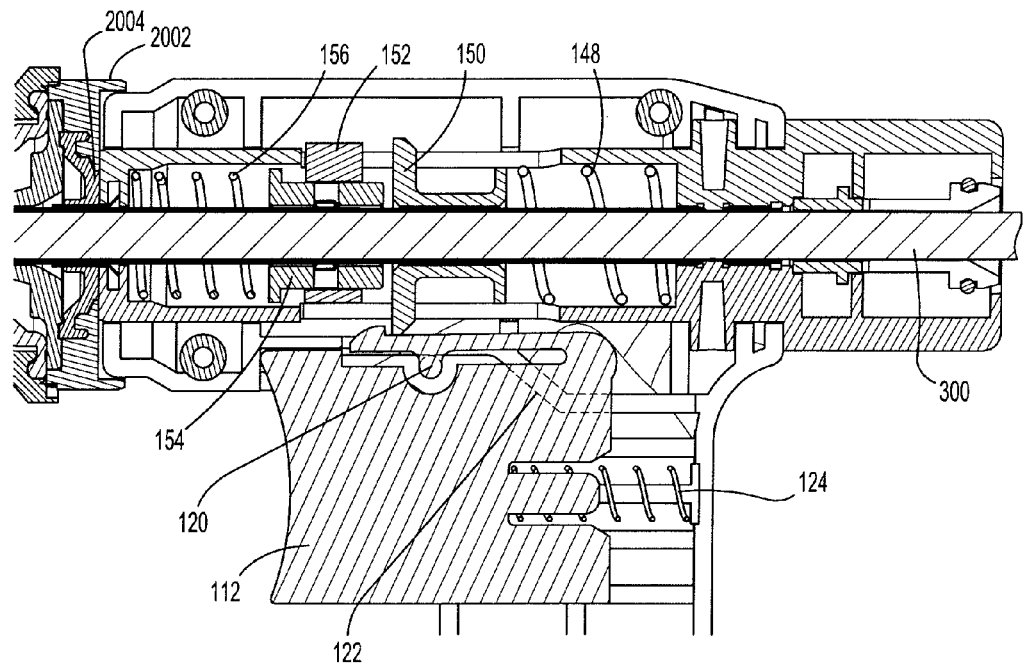
FIG. 15 is a side cross-sectional view illustrating the trigger of the obturator handle in an initial position.
Figure 16:
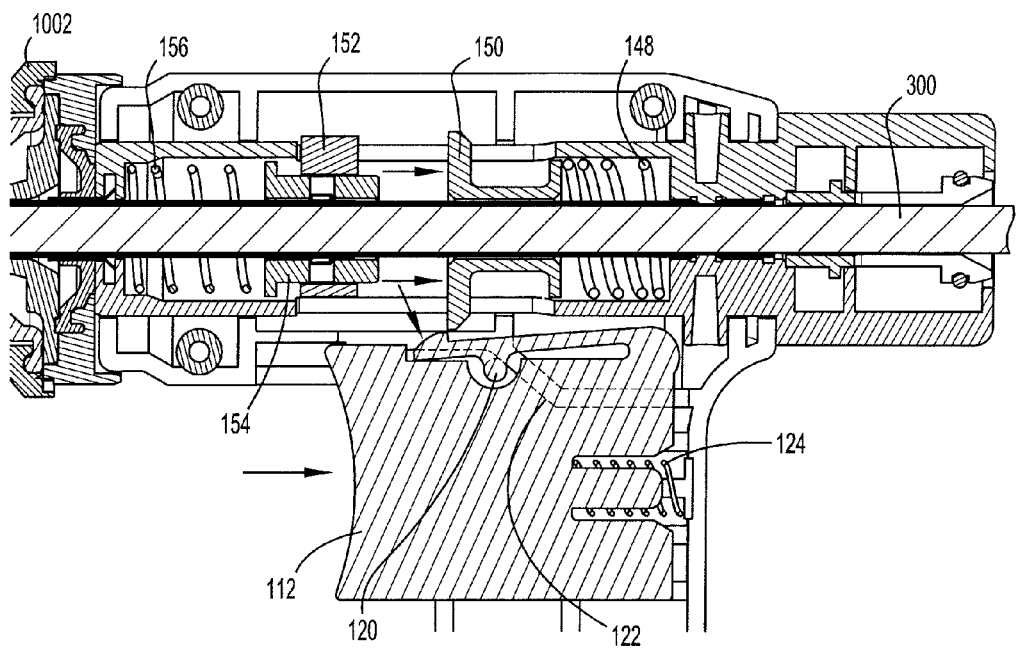
FIG. 16 is a side cross-sectional view illustrating the trigger of the obturator handle in an actuated position.

In operation and with initial reference to FIG. 15, trigger 112 is illustrated in the initial position with latch 116 of the trigger 112 engaging hammer 150 thereby preventing longitudinal movement of the hammer 150. This is the position achieved upon positioning of obturator cartridge 104 within handle 102. When it is desired to advance trocar system 10 within abdominal cavity, image transmitting member 190 of the trocar system is pressed against the tissue. Trigger 112 is depressed or retracted in the proximal direction as depicted in FIG. 16 which compresses hammer spring 148. Such movement of trigger 112 also causes latch 116 to pivot downwardly through movement of cam pin 120 against cam shelf 122 to thereby release hammer 150.

Figure 17:
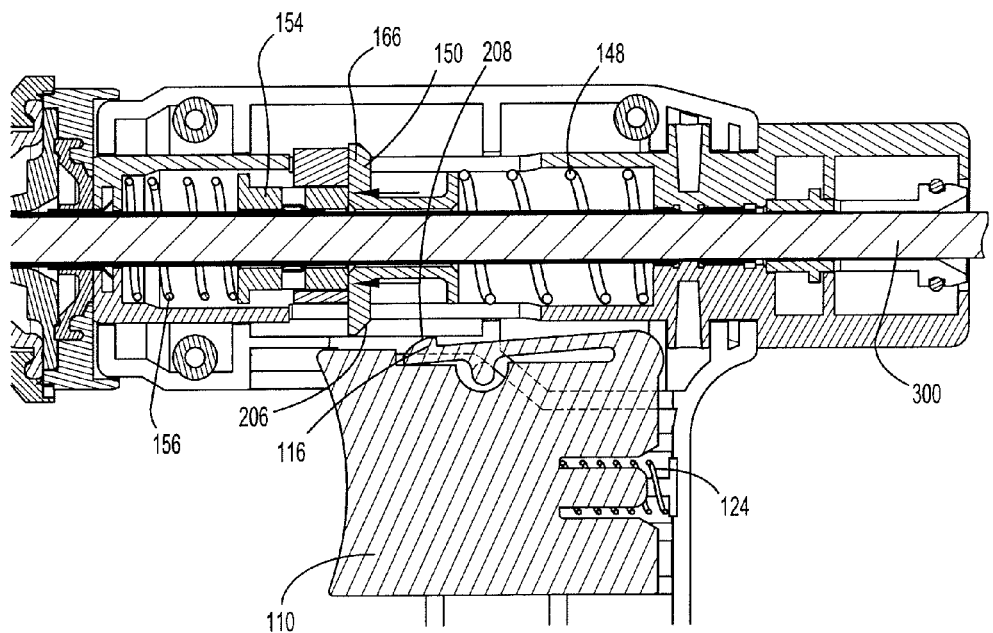
FIG. 17 is a side cross-sectional view illustrating the hammer of the obturator cartridge released to deploy the obturator blade.
Figure 18:
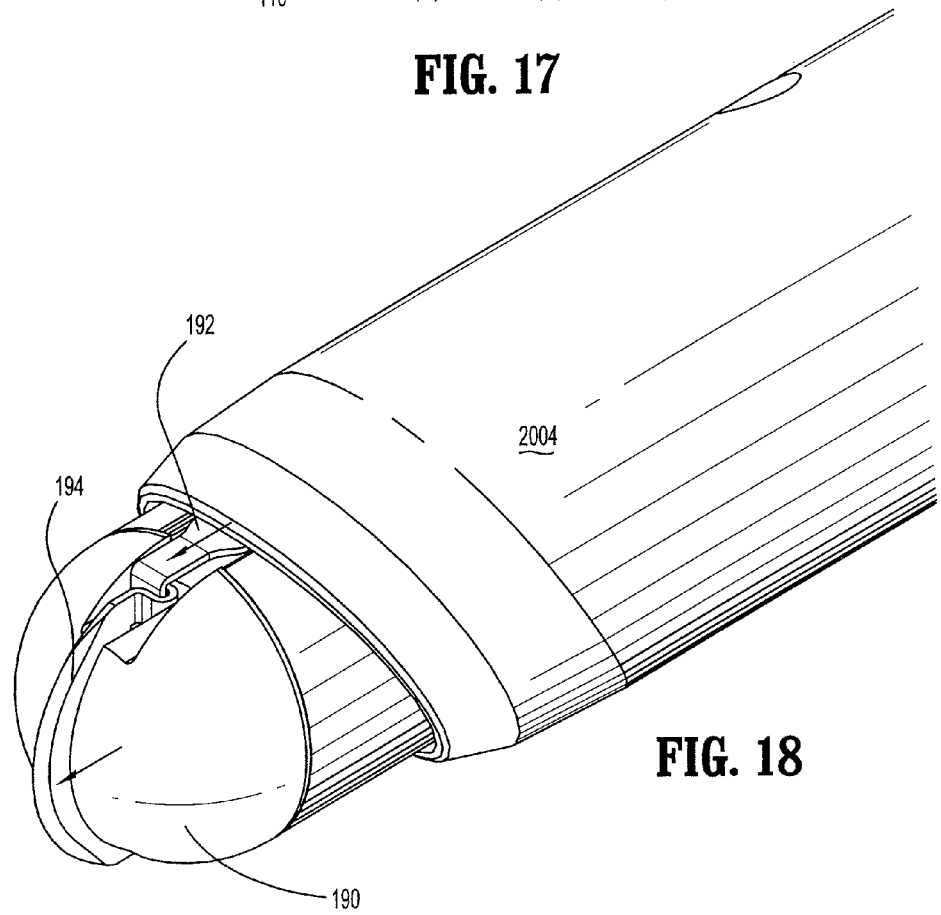
FIG. 18 is an enlarged perspective view illustrating the obturator blade deployed relative to the image transmitting member.

With reference to FIG. 17, hammer 150, which is no longer constrained by latch 116, is driven in a distal or firing direction by the linear force of compressed hammer spring 148 to contact driver holder 154 and correspondingly advance the driver holder 154. Distal advancement of driver holder 154 advances blade drivers 192 to advance relative to obturator member 134 which advances cutting blade 194 relative to image transmitting member 190. Advancing movement of driver holder 154 is limited by stop 152. In this advanced position depicted in FIG. 18, cutting blade 194 is positioned to penetrate, incise or cut through the tissue. Trigger 112 is released and returned to its initial position by trigger return spring 124.

Concurrently with advancing movement of driver holder 154, return spring 156 is caused to assume a compressed condition. The linear force of return spring thereby causes subsequent return of driver holder 154, blade drivers 192 and cutting blade 194 to the initial position of FIG. 15. During movement toward the initial position, driver holder 154 forces hammer 150 in a proximal direction and into engagement with latch 116 of trigger 112 to assume the initial condition. Proximal cam surface 206 of hammer 150 enable locking tabs 166 to ride along the corresponding cam surface 208 of latch 116 to facilitate securement of the locking tab 160 relative to the latch 116.

During penetration of the body tissue the surgeon either observes such penetration through the eyepiece of the endoscope 300, or in instances where a video system is utilized the surgeon simply observes the penetration of the body tissue via any known video monitor.

In operation, the surgeon may also more selectively deploy the cutting blade 194 during penetration. That is, the surgeon may insert the trocar assembly and bluntly penetrate the body tissue until reaching thicker tissue, such as muscle. At this point, the blade can be deployed to penetrate (cut through) this thick tissue, then retracted to provide blunt penetration until thick tissue is again encountered where once again the blade can be deployed.

After penetration into the body cavity, endoscope 300 may be removed and the obturator assembly 100 may be removed from the cannula assembly 1000, leaving the cannula assembly 1000 in the body for insertion of desired instrumentation therethrough.

Figure 19:
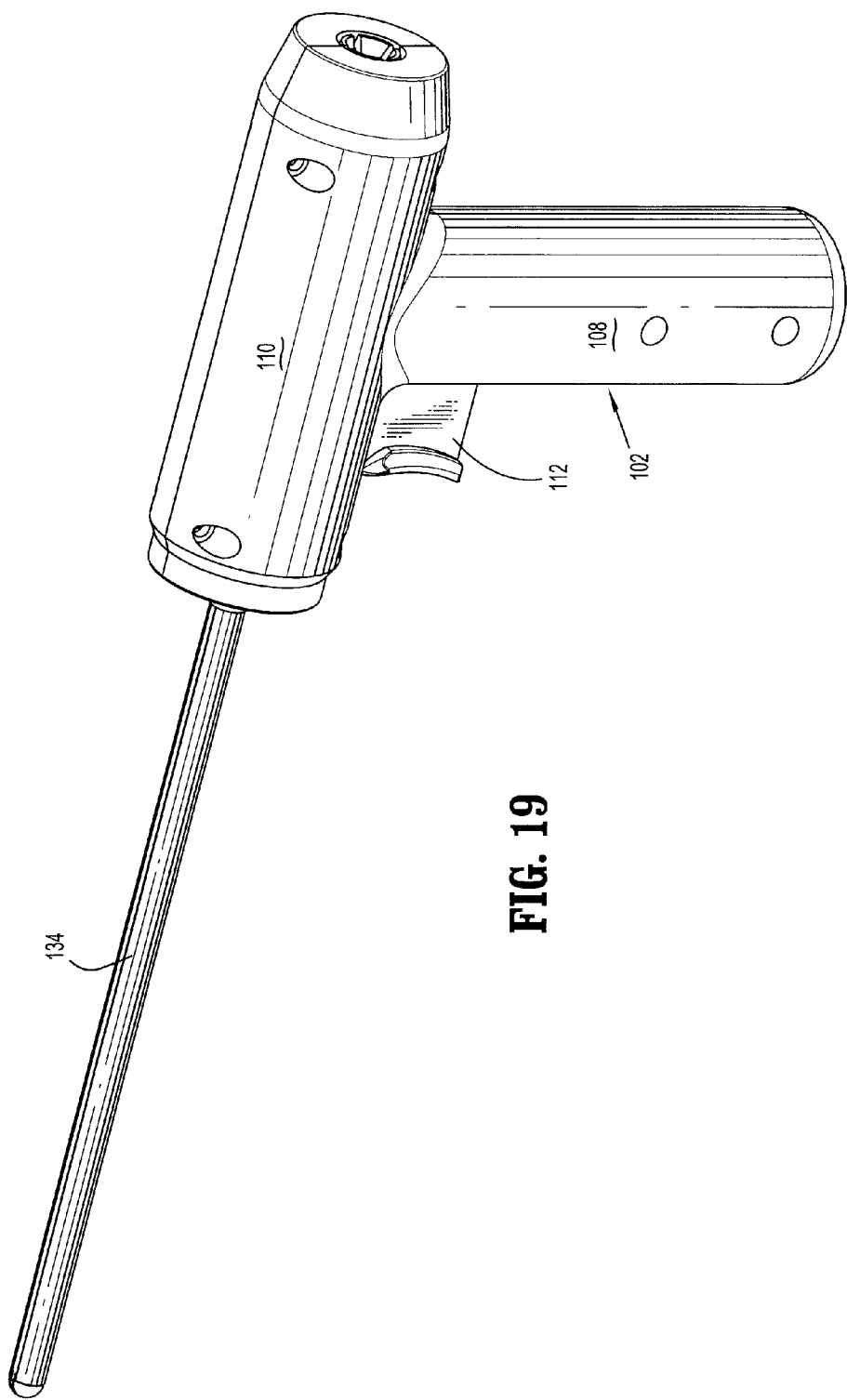
FIG. 19 is a perspective view illustrating an alternate embodiment of the obturator assembly.
Figure 20:
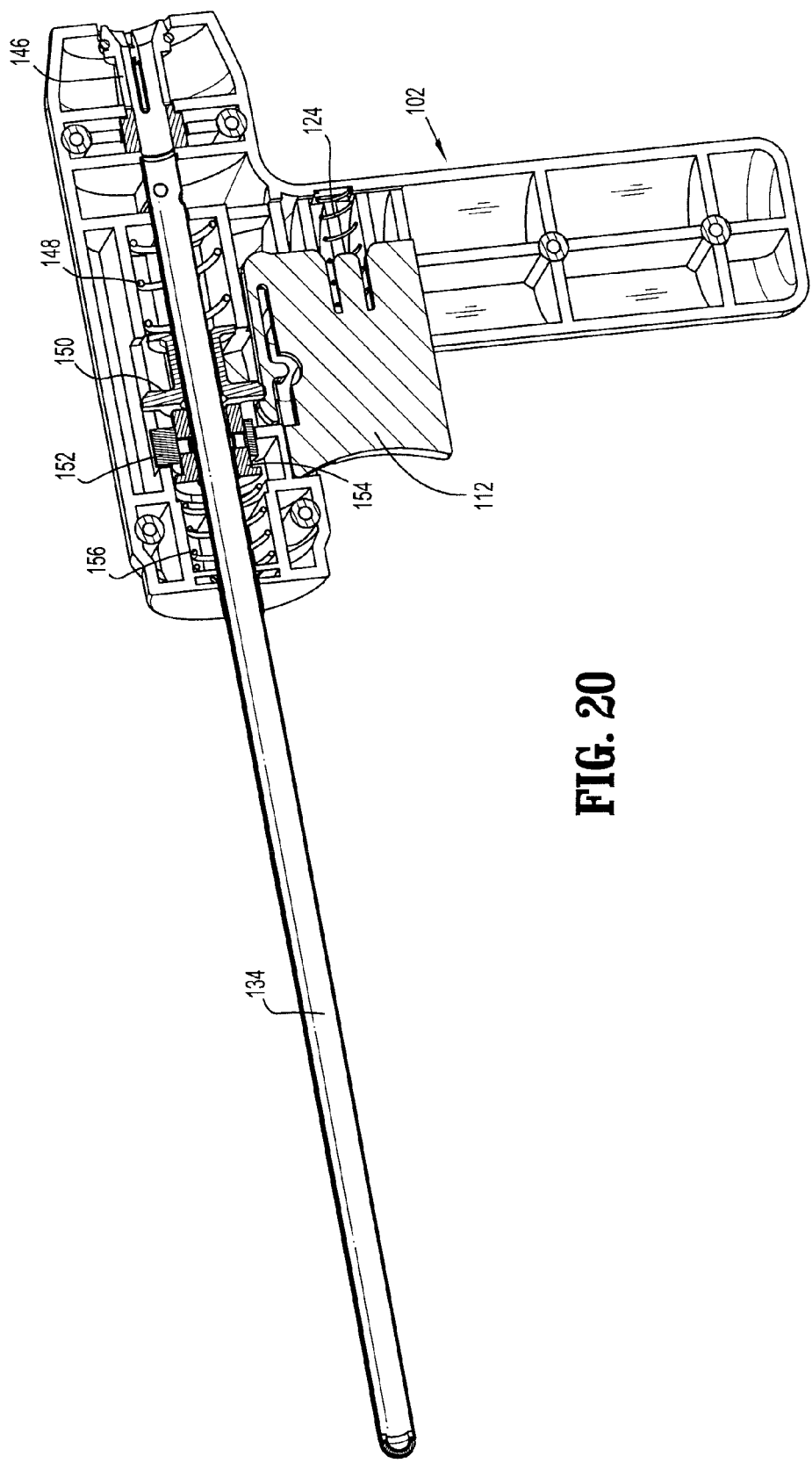
FIG. 20 is a perspective view in cross-section of the obturator assembly of FIG. 19.

FIGS. 19-20 illustrate another embodiment of the obturator assembly. This obturator assembly is similar to the embodiment of FIGS. 1-18; however, in accordance with this embodiment, obturator cartridge 104 and obturator handle 102 are a single unit, i.e., obturator cartridge 104 is not releasably mountable to obturator handle 102. Accordingly, obturator assembly 100 may be disposed of as a single unit or sterilized subsequent to its uses.

It will be understood that various modifications can be made to the embodiments of the present invention herein disclosed without departing from the spirit and scope thereof. For example, various diameters for the cannula assembly, the obturator assembly, as well as various diameter endoscopes are contemplated. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A trocar system, which comprises:
an obturator handle defining a handle axis and having an axial bore;
an obturator cartridge adapted for releasable mounting to the obturator handle, the obturator cartridge including:
a cartridge frame including a proximal portion extending proximally from the obturator handle when the obturator cartridge is mounted to the obturator handle; and
an elongate obturator extending distally from the cartridge frame and at least partially positionable within the axial bore of the obturator handle, the elongate obturator including an image transmitting member and having an obturator blade mounted adjacent the image transmitting member, the obturator blade adapted for movement relative to the image transmitting member between an initial condition and a deployed position; and
a trigger mounted to the obturator handle and adapted for releasable operative coupling to the obturator blade, the trigger movable to cause movement of the obturator blade from at least the initial condition to the deployed position thereof.

2. The trocar system according to claim 1 wherein the obturator cartridge includes a longitudinal opening extending through the cartridge frame and the elongate obturator, the longitudinal opening adapted to receive an endoscope.

3. The trocar system according to claim 2 wherein the cartridge frame of the obturator cartridge includes a firing member operatively engageable with the obturator blade and with the trigger, the firing member normally biased in a firing direction corresponding to the deployed condition of the obturator blade.

4. The trocar system according to claim 3 wherein the trigger includes a latch adapted to restrain the firing member in a first position corresponding to the initial condition of the obturator blade and wherein movement of the trigger causes release of the latch from the firing member to thereby permit the firing member to move in the firing direction toward a second position thereof.

5. The trocar system according to claim 4 wherein the cartridge frame includes a spring, the spring operatively couplable with the firing member and adapted to bias the firing member in the firing direction.

6. The trocar system according to claim 5 including a return spring disposed within the cartridge frame, the return spring positioned to engage the firing member upon movement of the firing member in the firing direction to the second position thereof, the return spring adapted to bias the firing member in a return direction opposed to the firing direction and to the first position of the firing member.

7. The trocar system according to claim 6 wherein the latch of the trigger is adapted to releasably couple with the firing member upon return thereof to the first position.

8. The trocar system according to claim 1 wherein the obturator cartridge includes a hammer member slidably disposed within the cartridge frame.

9. The trocar system according to claim 1 wherein the obturator cartridge includes a stop member fixedly disposed within the cartridge frame.

* * * * *